United States Patent
Nashner

[19]

[11] Patent Number: 6,010,465
[45] Date of Patent: *Jan. 4, 2000

[54] APPARATUS AND METHOD FOR CHARACTERIZING GAIT

[75] Inventor: Lewis M. Nashner, Lake Oswego, Oreg.

[73] Assignee: NeuroCom International, Inc., Clackamas, Oreg.

[*] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/790,564

[22] Filed: Jan. 29, 1997

Related U.S. Application Data

[62] Division of application No. 08/478,060, Jun. 7, 1995, Pat. No. 5,623,944, which is a division of application No. 08/138,374, Oct. 15, 1993, Pat. No. 5,474,087, which is a continuation of application No. 07/774,553, Oct. 10, 1991, abandoned.

[51] Int. Cl.$^7$ .................................................. A61B 5/10
[52] U.S. Cl. ............................................................. 600/595
[58] Field of Search .................................. 600/595, 587, 600/592

[56] References Cited

U.S. PATENT DOCUMENTS

| | | | |
|---|---|---|---|
| 4,122,840 | 10/1978 | Tsuchiya et al. | 600/592 |
| 4,416,293 | 11/1983 | Anderson et al. | 600/595 |
| 4,813,436 | 3/1989 | Au | 600/595 |
| 4,830,021 | 5/1989 | Thornton | 600/595 |
| 5,474,087 | 12/1995 | Nashner | 600/595 |
| 5,623,944 | 4/1997 | Nashner | 600/595 |

*Primary Examiner*—Michael Buiz
*Assistant Examiner*—Jonathan Goldberg
*Attorney, Agent, or Firm*—Bromberg & Sunstein LLP

[57] ABSTRACT

To characterize the gait of a subject, a treadmill having a movable support surface is provided with multiple transducers mounted beneath the movable support surface. The subject performs locomotion on the movable surface. The computer accepts a series of signals from each transducer and identifies the occurrence of heel-strike and toe-off. The computer identifies the subject's activity as walking or as running. The computer identifies two non-contiguous groups of transducers that are measuring a force greater than zero associated with the two feet and calculates quantities related to the forces exerted by each foot during each phase of walking or running.

6 Claims, 11 Drawing Sheets

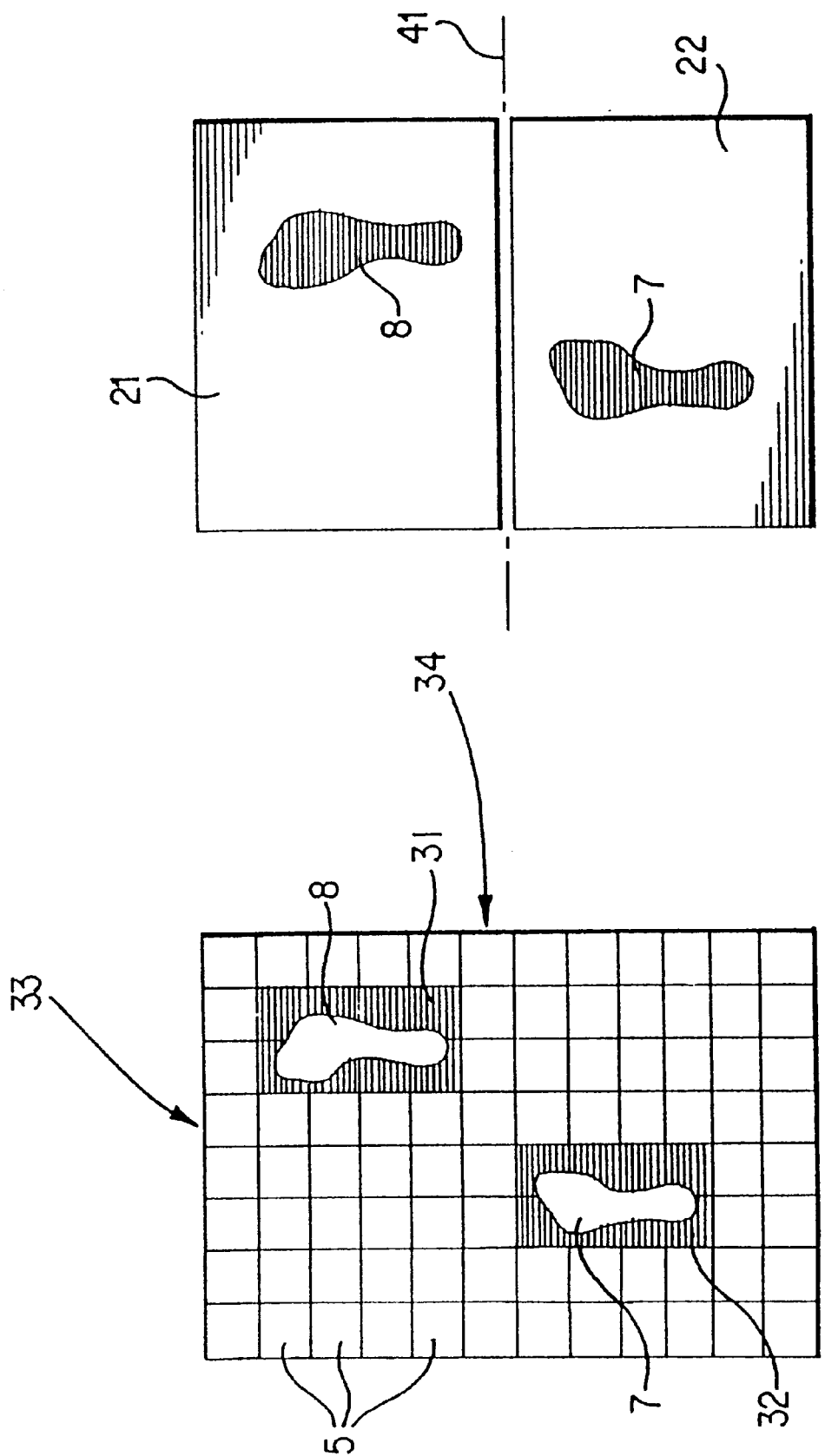

APPARATUS AND METHOD FOR CHARACTERIZING GAIT

RELATED APPLICATIONS

The present application is a divisional of application Ser. No. 08/478,060, filed Jun. 7, 1995 issued as U.S. Pat. No. 5,623,944, which is a divisional of application Ser. No. 08/138,374, filed Oct. 15, 1993, issued as U.S. Pat. No. 5,474,087, which in turn is a continuation of Ser. No. 07/774,553, filed Oct. 10, 1991, now abandoned. All of these applications are incorporated herein by reference.

TECHNICAL FIELD

The invention relates generally to an apparatus and method for characterizing gait by measuring the forces exerted on a support surface by the feet of a subject who is walking or running.

BACKGROUND OF THE INVENTION
Prior Art Methods for Characterizing Forces

Three methods have been described in the prior art for determining quantities related to the position, magnitude and distribution of the forces exerted by a subject's foot (or the two feet combined) against a support surface during standing or walking.

A. Coupled Force Transducers

One method described in the prior art is the forceplate, typically a flat, rigid surface which mechanically couples three but more often four linear force transducers. FIG. 15A shows a typical prior-art forceplate 20 with four force transducers 29, and FIG. 15B shows another prior-art forceplate 20 with only three force transducers. The following examples of published studies each describe a forceplate comprised of linear force transducers coupled to a substantially rigid plate to form a single force measuring surface, and each describes methods by which the force measuring surface is used to quantify aspects of the forces exerted by the feet of a subject standing on the forceplate; Nashner, L. M. (1970) "Sensory Feedback in Human Posture Control," Massachusetts Institute of Technology Report, MVT-70-3; Black, et al. (1978) "Computerized Screening of the Human Vestibulospinal System," Annals of Otology, Rhinology and Laryngology, 87:853–861; and Hassan, et al. (1990) "Effect of Loss of Balance on Biomechanics Platform Measures of Sway: Influence of Stance and Method of Adjustment," Journal of Biomechanics, 23:783–789. U.S. Pat. No. 4,136,682, to Pedotti, describes a substantially rigid platform, a plurality of force transducing members, and a hybrid processor for analyzing the space-time representation of the resultant forces exerted by a subject walking on the rigid platform. The most commonly determined quantities used to describe the forces exerted on the forceplate surface by an external body are the following: (1) the position (in the horizontal plane) of the center of the vertical axis component of force, (2) the magnitude of the vertical axis component of the center of force, and (3) the magnitude of the two horizontal axis components (anteroposterior and lateral) of the center of force. Calculation of position and magnitude quantities for the vertical axis component of the center of force requires that only the vertical force component be measured by each of the three (or four) mechanically coupled force transducers. To measure the horizontal axis components of force, the force transducers must also measure the horizontal plane components of force.

The exact form of the calculations required to determine the above described center of force position and magnitude quantities from the measurement signals of the linear force transducers depends on the number and positions of the force transducers. Specifically, these algorithms must take into account the known distances between the force measuring transducers. Algorithms for performing such calculations are well documented in the prior art. The Operators Manual for the EquiTest system manufactured by NeuroCom International, Inc. of Clackamus, Oreg., the assignee herein, for example, describes mathematical formulae for calculating the position (anteroposterior and lateral components) and the magnitude of the vertical axis component of the center of force exerted on a mechanically coupled 4-transducer forceplate. Also described are the calculations necessary to determine the magnitude of the horizontal axis (anteroposterior component) of the center of force using an additional linear force transducer with sensitive axis in the anteroposterior horizontal axis of the forceplate. A more complex forceplate manufactured by Advanced Mechanical Technologies, Inc. of Newton, Mass., uses mechanically coupled multi-axis force transducers to measure all of the vertical axis, longitudinal horizontal axis, and lateral horizontal axis force components.

When a forceplate is used to measure quantities related to the position of the center of force, the position quantity is always determined in relation to coordinates of the forceplate surface. If the position of the foot exerting the force on the surface is not precisely known in relation to the forceplate surface, or if the position of the foot changes with time relative to the surface, the position of the center of vertical force cannot be determined in relation to a specified anatomical feature of the foot.

B. Instrumented Shoe

A second method described in the prior art for measuring quantities related to forces exerted by a foot 10 against a supporting surface during standing and walking is a shoe in which the sole is instrumented with linear force transducers. One example of a system incorporating force measuring transducers in a shoe is the Computer Dyno Graph (CDG) System manufactured by Infotronic Medical Engineering of Tubbergen, The Netherlands. Other examples of systems incorporating force measuring transducers into a shoe was described in Spolek, et al. (1976) "An Instrumented Shoe. A Portable Force Measuring Device," Journal of Biomechanics 9:779–783 and Ranu, H. S. (1987) "Normal and Pathological Human Gait Analysis Using Miniature Triaxcial Shoe-Borne Load Cells," American Journal of Physical Medicine 66:1–10. The principles for determining the position of the center of vertical force exerted on the sole of the shoe by the subject's foot are mathematically similar to those used to calculate the position of the center of force quantities using the forceplate.

Because the position of an instrumented shoe is fixed in relation to the foot, the instrumented shoe can be used to determine the position of the center of vertical force in relation to coordinates of the foot, regardless of the position of the foot on the support surface. A disadvantage of the instrumented shoe is that the position of the center of vertical force cannot be determined in relation to the fixed support surface whenever the position of the foot on the support surface changes during the measurement process. Another disadvantage in a clinical environment is that the subject must be fitted with an instrumented shoe.

C. Independent Force Transducers

A fundamentally different method described in the prior art for determining quantities related to the forces exerted on a support surface utilizes a plurality of mechanically independent vertical force transducers. Each vertical force transducer measures the total vertical force exerted over a small sensing area. The independent transducers are arranged in a matrix to from a force sensing surface. The two-dimensional position in the horizontal plane and the magnitude of the vertical component of the center of force exerted on the sensing surface can be determined from the combined inputs of the mechanically independent transducers. When the vertical force transducers are not mechanically coupled, however, the accuracy of the center of vertical force position quantity will be lower, and depends on the sensitive area of each transducer and on the total number and arrangement of the transducers. When mechanically independent vertical force transducers are used to determine the position of the center of vertical force, the resulting quantities are determined in relation to coordinates of the force sensing surface. Two examples of systems which use grids of independent force or pressure measuring transducers to map the distribution of forces during human gait analysis are the F-Scan system described in an article by Podoloff, R. M. (1991) "A Pressure Mapping System for Gait Analysis," Sensors, May, 1991, pp.21–25 and the Peruchon, et al. (1990) "Individual Gait Characterization from Dynamic Analysis of Plantar Force Distribution" in: Brandt, et al. (eds.) *Disorders of Posture and Gait*, George Thieme Verlag, N.Y., pp. 62–66.

The plurality of independent force measuring transducers can be used to determine additional quantities related to the distribution of forces exerted against a support surface by a subject's foot. FIG. 5 in the Podoloff article and FIG. 3 in the Peruchon, et al. article show examples of the outlines that can be produced by a system for mapping the distribution of pressures exerted by the foot on the surface. As described in the articles, the positions of anatomical features of the foot such as the heel, the ball, and the toes can be identified form the foot pressure maps. When the position of a first anatomical feature is determined in relation to the support surface by the pressure mapping means, the position of a second anatomical feature of the foot can be determined in relation to the support surface by the following procedure. The linear distance between the first and second anatomical features is determined. Then, the position of the second anatomical features in relation to the support surface is determined to be the position of the first anatomical feature in relation to the support surface plus the linear distance between the first and second anatomical features.

Measurement of Support Surface Reaction Forces

When a subject stands with a foot placed in a fixed position on the surface of a force sensing surface, the position of the center of force exerted by the foot can be determined in relation to coordinates of the forceplate surface. If the position of a specified anatomical feature of the foot (for example, the ankle joint) is also known in relation to the coordinates of the forceplate surface, the position of the center of force in relation to coordinates of the specified anatomical feature of the foot can be determined by a coordinate transformation in which the difference between the force and anatomical feature position quantities are calculated.

Analysis of Support Surface Reaction Forces During Gait

Forceplates, instrumented shoes and independent force transducers have all been used in the prior art to measure quantities related to the position and magnitude of the center of force exerted by each foot against the support surface during stepping-in-place, walking, and running. Forceplates embedded in walkways have measured quantities related to the position and magnitude in relation to the fixed (forceplate) support surface for single strides during overground walking and running (for examples; Nashner, L. M. (1980) "Balance Adjustments of Humans Perturbed While Walking," J. Neurophysiol. 44:650–664; Andriacchi, et al. (1977) "Walking Speed as a Basis for Normal and Abnormal Gait Measurements," Journal of Biomechanics 10:261–268; and Winter, D. A. (1980) "Overall Principle of Lower Limb Support During Stance Phase of Gait," Journal of Biomechanics 13:923–927). Using additional information on the position of a specified anatomical feature of the foot in relation to the forceplate support surface, the position of the center of force has also been determined in relation to a specified anatomical feature of the foot.

The position and the magnitude of the center of force exerted by a foot against the support surface have been determined relative to anatomical features of the foot by embedding force transducers in the shoes of walking and running subjects (for examples, Ranu, Podoloff and Spolek). Measures of the timing of heel-strikes and toe-offs have been made using contact switches embedded in the subject's shoes (Ishida, et al. (1990) "Evaluation on the Stepping Movement with a Recording of Plantar Switching" in: Brandt, et al. (eds.) *Disorders of Posture and Gait*, George Thieme Verlag, N.Y., pp. 58–61).

Categories of Gait

The phases of human gait have been described by many authors; for examples, Inman, et al. (1981) "Human Walking," Williams and Wilkins, Baltimore; Winter, D. A. (1983) "Biomechanical Motor Patterns in Normal Walking," Journal of Motor Behavior 15:302–330; and Winestein, et al. (1989) "Quantitative Dynamics of Disordered Human Locomotion: a Preliminary Investigation," Journal of Motor Behavior 21:373–391.) Human gait may be classified in general categories of walking and running. During walking, at least one foot is always in contact with the support surface and there are measurable periods of time greater than zero during which both feet are in contact with the support surface. During running, there are measurable periods greater than zero during which time neither foot is in contact with the support surface and there are no times during which both feet are in contact with the support surface.

Walking can be separated into four phases, double support with left leg leading, left leg single support, double support with right leg leading, and right leg single support. Transitions between the four phases are marked by what are generally termed "heel-strike" and "toe-off" events. The point of first contact of a foot is termed a "heel-strike", because in normal adult individuals the heel of the foot (the rearmost portion of the sole when shoes are worn) is usually the first to contact the surface. However, heel-strike may be achieved with other portions of the foot contacting the surface first. During running normal adult individuals sometimes contact with the ball of the foot (forward portions of the sole when shoes are worn). Individuals with orthopedic and/or neuromuscular disorders may always contact the surface with other portions of the foot or other points along the perimeter of the sole when shoes are worn. Similarly, while the ball and toes of the foot are the last to contact the surface at a toe-off event in normal adults, a patient's last point of contact may be another portion foot. Thus, regardless of the actual points of contact, the terms heel-strike and toe-off refer to those points in time at which the foot first contacts the support surface and ceases to contact surface, respectively.

Characterization of Gait Using a Treadmill

Treadmills allowing a subject to locomote over a range of walking and running speeds within a confined space have been described in the prior art (Traves, et al. (1983) "A Speed-Related Kinematic Analysis of Overground and Treadmill Walking" in: Winter, et al. (eds.) *Biomechanics XI*, Human Kinetics Publishers, Champaign, pp. 423–426; Nelson, et al. (1972) "Biomechanics of Overground Versus Treadmill Running," Medicine and Science in Sports 4:233–240; and Charteris, et al. (1978) "The Process of Habitation to Treadmill Walking: a Kinetic Analysis," Perceptual and Motor Skills 47:659–666). A treadmill allows the difficulty of gait to be precisely set by independently controlling the belt speed and the inclination of the belt. The subject can be maintained in a fixed position relative to the measuring surface underlying the treadmill belt by coordinating the speed of gait with the speed of the treadmill belt movement.

Several prior art research studies have described treadmills in which a single forceplate with mechanically coupled force transducers has been mounted directly beneath the treadmill belt. Kram et al., in their paper "A Treadmill-Mounted Force Platform", Journal of The American Physiological Society, 1989, pages 1692–1698, describe a treadmill having a single forceplate. This paper is enclosed herewith and hereby incorporated herein by reference. The single forceplate provided continuous measurement of the forces exerted by the combined actions of the two feet on the overlying treadmill belt during gait.

It is sometimes desirable to determine the position of the center of force in relation to coordinates of specified anatomical features of the foot when the foot is in contact with a surface which is moving in relation to a fixed force sensing surface. This occurs, for example, when the foot is contacting the moving belt of a treadmill which overlays a force sensing surface. To determine the position of the center of force in relation to coordinates of the specified anatomical features of the foot, two coordinate transformations are performed. One, the position of the center of force is determined in relation to coordinates of the moving treadmill belt. Two, the position of the moving treadmill belt is determined in relation to coordinates of the specified anatomical feature of the foot. To perform the first of these coordinate transformations requires knowledge of the treadmill belt position in relation to the fixed force sensing surface position on a continuous basis. To perform the second of these two coordinate transformations requires knowledge of the position of the specified anatomical features of the foot in relation to the treadmill belt. Since the position of the foot and its anatomical features does not change in relation to the treadmill belt following each heel-strike event and before the subsequent toe-off of that foot, the position of the specified anatomical features of the foot needs be determined only once at heel-strike for each step.

One method to determine the position of the treadmill belt on a continuous basis in relation to the fixed force sensing surface is to use one of several sophisticated commercial treadmill systems described in the prior art which measure the anteroposterior speed of the moving treadmill belt on a continuous basis, and which provide the means to regulate the belt anteroposterior speed on a continuous basis. One example of a commercially available treadmill system with automatic speed control and belt speed measurement systems is the Star Trac 2000, manufactured by Unisen, Inc., Tustin, Calif. When one of these treadmill systems is used, the information necessary to determine the continuous position of the treadmill belt in relation to the underlying forceplate is obtained by performing mathematical integration of the belt speed signal on a continuous basis.

There are methods described in the prior art which can be used to determine, at the time of heel-strike, the position of the moving treadmill belt in relation to the specified anatomical features of the foot. One method is to use one of several commercially available optical motion analysis systems. Two examples of commercially available motion analysis systems which describe applications for tracking the motions of identified points on the human body during locomotion include the ExpertVision system manufactured by MotionAnalysis Corp., Santa Rosa, Calif. and the Vicon system manufactured by Oxford Medilog Systems, Limited, Oxfordshire, England. In accordance with this method, one or more optical markers are placed on the specified anatomical features of the foot. One or more additional markers are placed on the treadmill belt at predetermined positions. The number and placement of the optical markers on the anatomical feature and the treadmill belt determine the accuracy of the measurement as specified by the systems manufacturers. At the time of heel-strike, the positions of the treadmill belt marker or markers are then determined in relation to the positions of the anatomical feature marker or markers in accordance with methods specified by the system manufacturer.

The prior art has not described devices and methods for separately determining quantities related to the force exerted by each foot against the treadmill belt support surface at all phases of the step cycle, nor has the prior art described a means for determining quantities related to the position of the center of force exerted by each foot in relation to a fixed point on the treadmill belt or in relation to a specified anatomical feature of the foot or to train normals to alter their gait patterns.

SUMMARY OF THE INVENTION

The present invention provides in a first preferred embodiment an apparatus and method for characterizing the gait of a subject, and employs a treadmill having a movable support surface with multiple transducers, which may be forceplates, independently mounted beneath the movable support surface. The apparatus and method also uses a computer for accepting and processing output signals from the transducers. The subject is instructed to perform locomotion on the movable surface. The computer accepts a series of output signals from each transducer and determines, for each point in time, the anteroposterior position of the foremost forceplate whose output signal is indicative of a non-zero force. The computer identifies the occurrence of a heel-strike event when the anteroposterior position of the foremost forceplate having non-zero force is located a greater distance forward than the foremost forceplate having non-zero force for the immediately preceding point in time. Alternatively, the computer identifies the occurrence of a heel-strike event when the force exerted on the foremost forceplate increases above a zero value after having been at a zero value for more than a predetermined period of time. The computer also determines, for each of a series of heel-strike events, the average lateral position of the center of vertical force, identifying the odd numbered heel-strike events as "left heel-strike events" (or "right heel-strike events") if the average lateral position of the center of force for odd numbered heel-strike events is determined to be to the left (or right) of the average lateral position of the center of force for even numbered heel-strike events. The process of "characterizing" the gait of a subject as that term is used in the claims below involves at a minimum separately identifying heel-strike events and/or toe-off events associated with the gait of the subject. The computer identifies the locomotor activity as walking during a period of time if the scanned output signals are never zero during that period. The computer identifies the locomotor activity as running during a period of time if the sum of the output signals is zero for a measurable interval of time during that period. The computer identifies two non-contiguous groups of transducers that are measuring a force greater than zero to identify forces associated with each of the two feet separately and calculates quantities related to the forces exerted by each foot during each phase of walking or running. The quantities may be located with respect to the treadmill or to the anatomical features of the foot. A plurality of contact sensitive transducers disposed in fixed relation to the subject's foot are used to locate the quantities with respect to anatomical features of the foot.

BRIEF DESCRIPTION OF THE DRAWINGS

FIG. 3 shows the feet on the belt and multiple transducers under each foot.

FIG. 4 shows the feet on a two-forceplate treadmill.

DETAILED DESCRIPTION OF SPECIFIC EMBODIMENTS

The present invention provides in a preferred embodiment an apparatus and method utilizing two or more independent force measuring arrangements configured to measure the forces exerted on the support surface beneath the moving belt of a treadmill. The subject is instructed to perform a locomotor activity on the moving treadmill belt, and the embodiment determines on a continuous basis, and during all phases of the locomotor activity, quantities related to the position and the magnitude of the center of force exerted by each foot separately on the belt surface of the treadmill.

Figure 1:
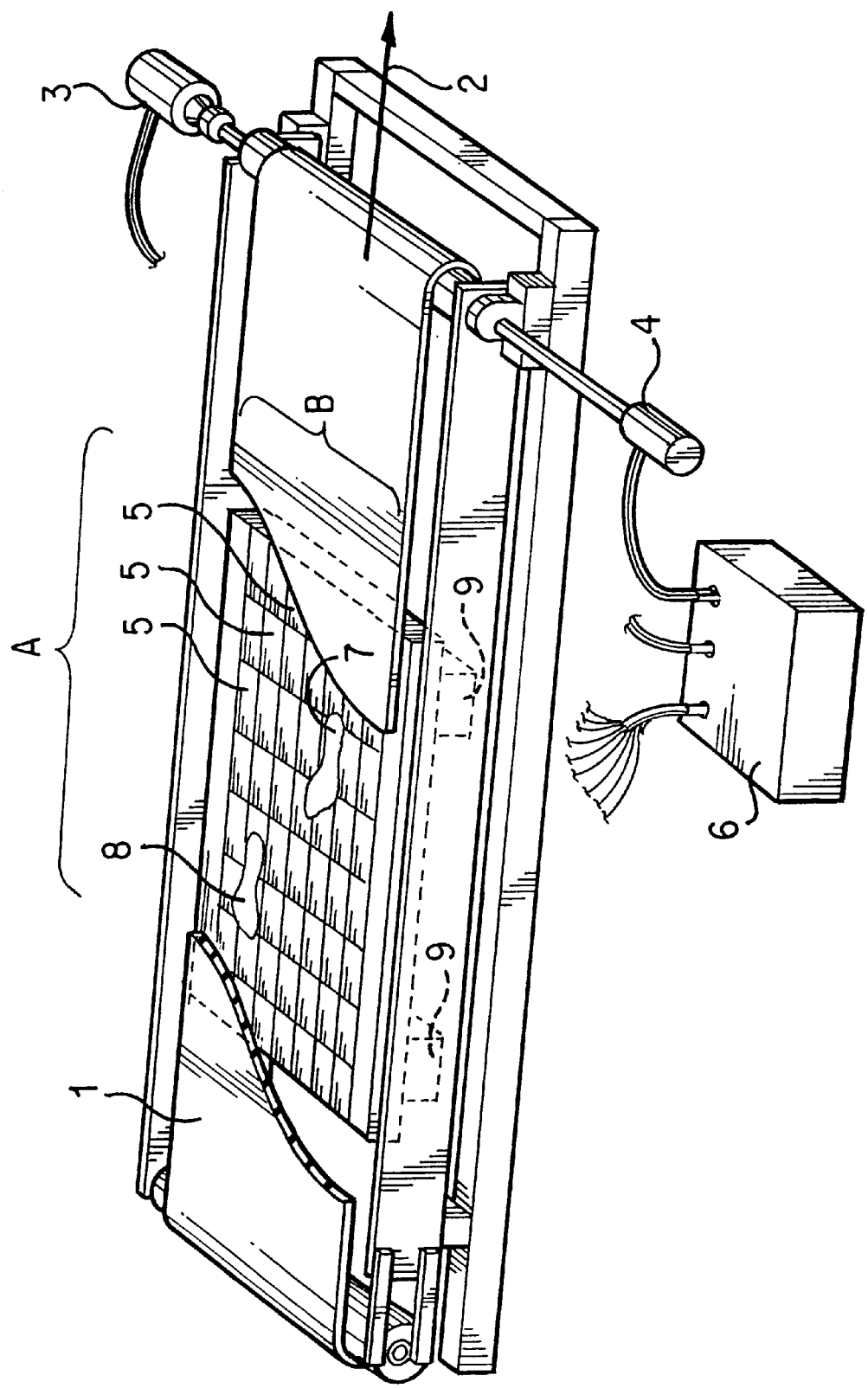
FIG. 1 shows a treadmill with a plurality of transducers underneath the moving belt.

A first preferred embodiment of the apparatus of the invention having a plurality of transducers is shown in FIG. 1. In this embodiment, the subject performs a locomotor activity on a treadmill belt 1 movable along the subject's anteroposterior axis 2, i.e., along the length of the treadmill belt 1. The belt is driven by a motorized drive system 3. The anteroposterior position of the treadmill belt is measured on a continuous basis by a rotary potentiometer 4 or other position measuring system. A plurality of mechanically independent vertical force transducers 5 are placed beneath the treadmill belt. Contact sensitive transducers (131 in FIG. 13) may be fitted to the subject's foot or shoe as part of a system for determining the position on the foot of the center of force at the time of heel-strike. A computer 6 receives information from the rotary potentiometer 4, from each of the plurality of transducers 5, and from the contact sensitive transducers 131, and then executes computational algorithms described hereinbelow to determine quantities related to the following:

(1) the phase of the step cycle of the locomotor activity,
(2) the classification of the locomotor activity as walking or running,
(3) the position and the magnitude of the center of force exerted by each foot in relation to coordinates of the plurality of independent force transducers,
(4) the position and the magnitude of the center of force exerted by each foot in relation to coordinates of the movable treadmill belt, and
(5) the position and the magnitude of the center of force exerted by each foot in relation to a specified anatomical feature of the foot.

Figure 2:
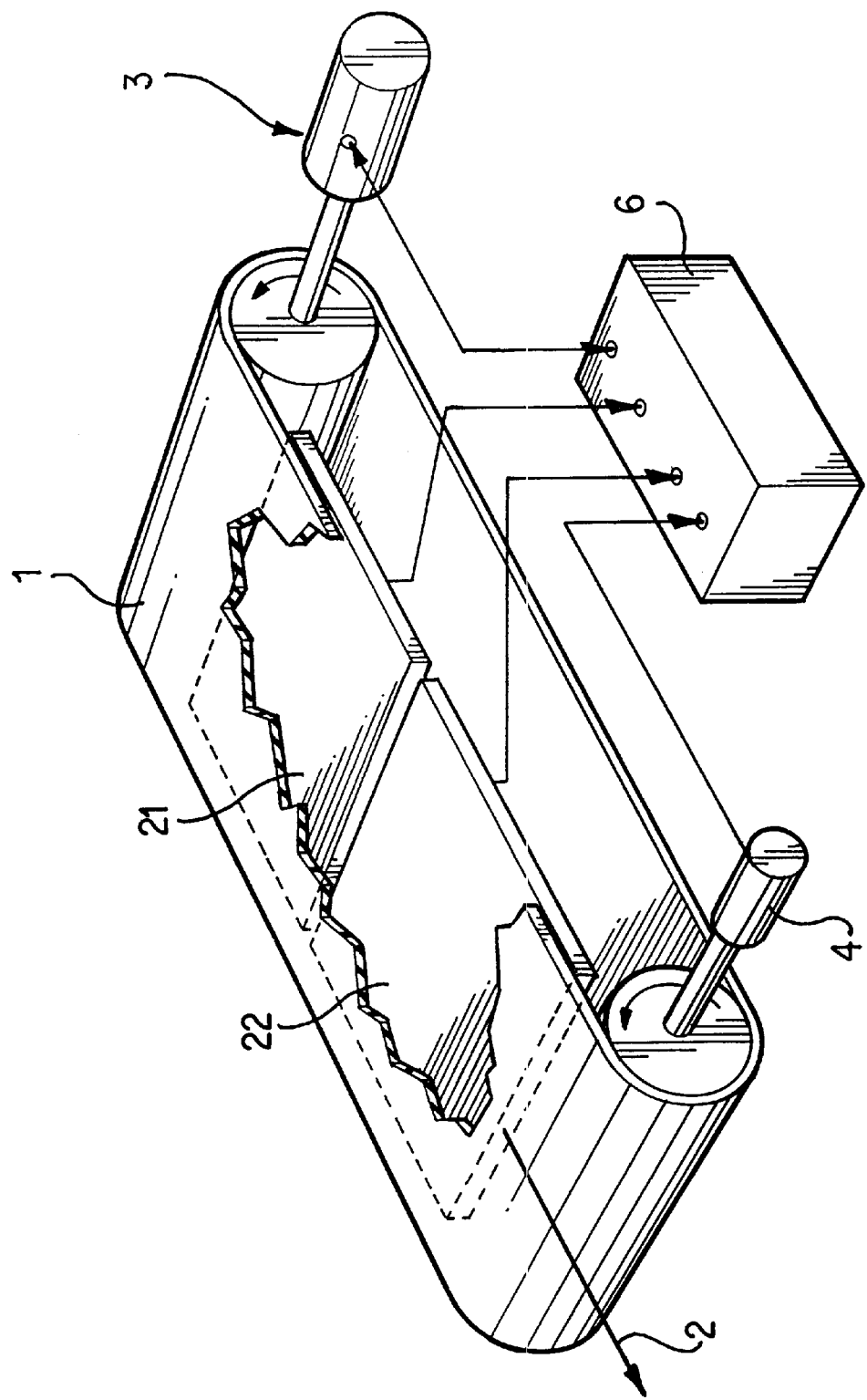
FIG. 2 shows a treadmill with two forceplates underneath the moving belt.

A second preferred embodiment of the invention having a pair of forceplates is shown in FIG. 2. Using the second preferred embodiment, the subject performs a locomotor activity on a treadmill belt 1 movable along the longitudinal axis 2. The belt is driven by motorized drive system 3. The anteroposterior position of the treadmill belt is monitored on a continuous basis by a position measuring system 4. Two independent forceplates, for measuring the position and the magnitude of the center of force, are placed beneath the treadmill belt. The first forceplate 21, termed the "Heel-Strike" forceplate, is a forceplate with mechanically coupled linear force transducers which is located beneath the forward area of the treadmill belt. The second forceplate 22, termed the "Toe-Off" forceplate, is a forceplate with mechanically coupled linear force transducers which is located beneath the rear area of the treadmill belt. Contact sensitive transducers (131 in FIG. 13) may be fitted to the subject's foot or shoe as part of a system for determining the position on the foot of the center of force at the time of heel-strike. A computer 6 receives information from the rotary potentiometer 4, from the Heel-Strike and Toe-Off forceplates 21 and 22 respectively, and from the contact sensitive transducers 131, and then executes computational algorithms described hereinbelow to determine quantities related to the following:

(1) the phase of the step cycle within the locomotor activity,
(2) the classification of the locomotor activity as walking or running,
(3) the position and the magnitude of the center of force exerted by each foot in relation to coordinates of the Heel-Strike and Toe-Off forceplates,
(4) the position and the magnitude of the center of force exerted by each foot in relation to coordinates of the movable treadmill belt.

In FIG. 1 the movable belt 1 is partially cut away to show the transducers 5 mounted directly beneath a tread area indicated by the brackets A and B. The transducers, in this embodiment an array of independently-mounted transducers, may be supported by a common support structure 9. In the embodiment of FIG. 1, each transducer is associated with the portion of tread area directly above it such that force exerted by the foot on the belt within a given portion of tread area is wholly transferred to the transducer beneath that portion of tread area. A single portion of tread area corresponds to one of the small squares 5. FIG. 3 shows a top view of the treadmill transducers bracketed by A and B of FIG. 1. As can be seen in FIGS. 1 and 3, the transducers 5 are arranged in a matrix, and the area of each portion of the tread area corresponding to a transducer 5 is less than the area of the soles of the subject's feet. In FIG. 3, the position on the belt of the two feet in a "walking double support right foot leading" position is indicated by 7 and 8.

The present invention also provides a third preferred embodiment apparatus and method utilizing the apparatus of the first preferred embodiment and contact sensitive transducers fitted to the foot, or to the sole when shoes are worn, to determine on a continuous basis the center of force position in relation to coordinates of a specified anatomical feature of the foot.

Figure 13:
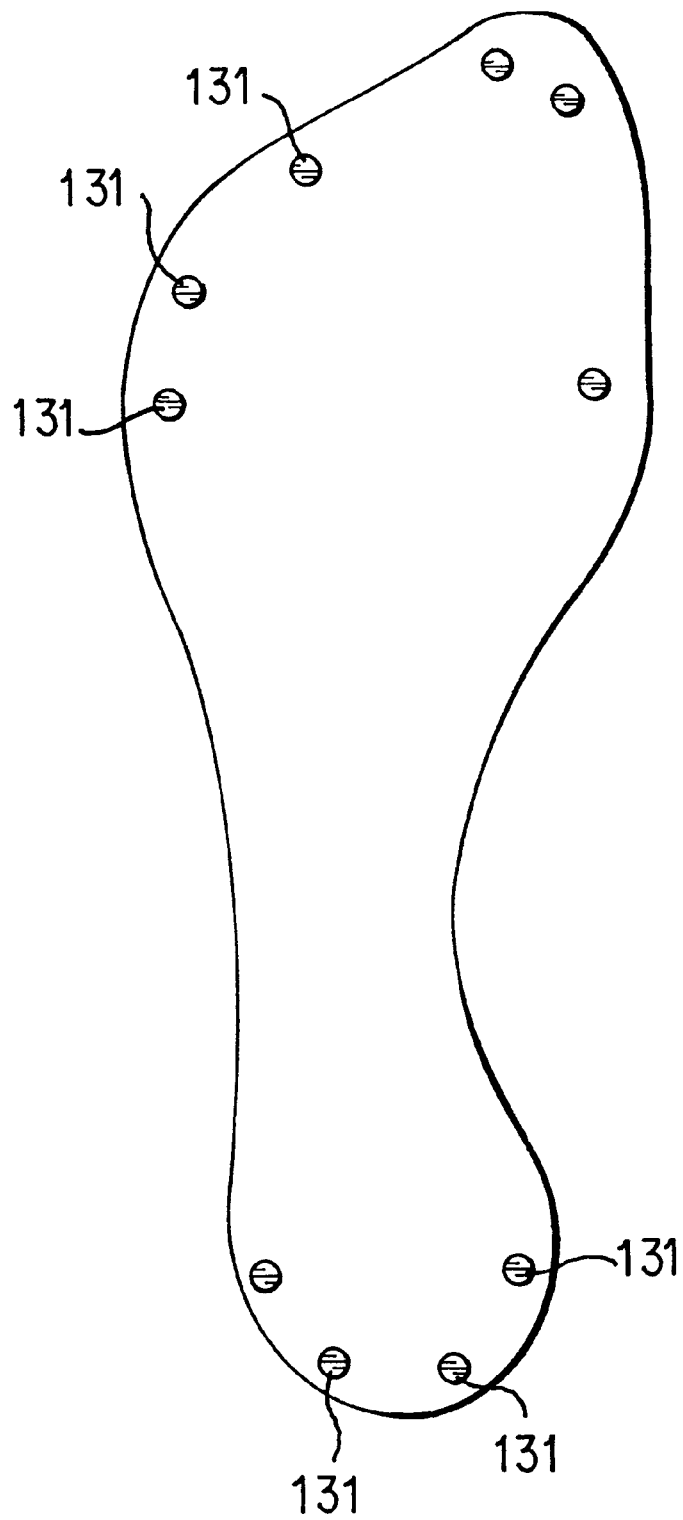
FIG. 13 shows a shoe fitted with contact sensitive transducers.

The method for determining on a continuous basis the center of force position in relation to coordinates of a specified anatomical feature of the foot is based on the fact that, between heel-strike and toe-off, the foot is stationary with respect to the moving belt. This means that if the position of the foot at heel-strike is known with respect to the force measuring system, then by coordinate transformation it may be known with respect to the belt and by further coordinate transformation it may be known with respect to a specified anatomical feature of the foot. In the third preferred embodiment, the present invention uses contact sensitive transducers to determine the position of the foot at the heel-strike. FIG. 13 shows the sole of a shoe instrumented with contact sensitive transducers 131.

Mounting points are located at the likely first points of contact at heel-strike. The mounting position of each contact sensitive transducer is determined in relation to the specified anatomical features of the foot. The second embodiment also includes a position measuring system for measuring the position of the moving treadmill belt on a continuous basis in relation to the fixed force sensing transducers underlying the treadmill belt. In addition to the force sensing transducers, the computer accepts and processes signals from the plurality of contact sensing transducers and the treadmill belt position measuring system.

Analysis of Support Surface Reaction Forces

When a subject's foot is in contact with that portion of the treadmill belt laying over a single forceplate and the position of the belt moves in relation to the coordinates of the forceplate surface, the position of the center of force is determined in relation to coordinates of the fixed forceplate surface. To determine the position of the center of force in relation to coordinates of the moving treadmill belt, a transformation from coordinates of the fixed forceplate surface to coordinates of the moving treadmill belt requires additional quantities related to the position of the moving treadmill belt in relation to the fixed forceplate surface.

In some situations, portions of the subject's foot are simultaneously in contact with two independent but immediately adjacent forceplate surfaces, and therefore the foot exerts a fraction of the total force on each forceplate. In these situations, the position and magnitude of the center of the total force exerted by the foot are not determined by the positions and magnitudes of the center of force exerted on each forceplate separately. To determine the position and magnitude quantities for the center of the total force exerted by the foot, an additional calculation combines the independent position and magnitude quantities into one total position and magnitude quantity.

Clinical Utility for Methods for Measuring Reaction Forces

In the clinical assessment and training of gait, although not provided by the prior art, it would be desirable to be able to determine, through all phases of the step cycle and for successive steps, quantities related to the position and the magnitude of the center of force exerted by each foot separately against the support surface. Knowledge of these quantities in relation to specified anatomical features of the foot could be used to determine the torsional moments and the loads exerted on the ankle joint and other anatomical features of the leg. Knowledge of these position and magnitude quantities in relation to the support surface could be used to determine stride length, stride width, magnitude of heel-strike impact and the stability of the gait.

Measuring Reaction Forces In Relation to Specified Anatomical Features of the Foot It is sometimes desirable to determine the position of the center of force in relation to coordinates of one or more specified anatomical features of the foot. To transform the center of force position quantity from coordinates of the moving treadmill belt into coordinates of each of the specified anatomical features of the foot, it is first necessary to determine the position of the moving treadmill belt in relation to coordinates of each of the specified anatomical features of the foot. One method is described hereinabove, under Background of the Invention, for determining the position of the moving treadmill belt in relation to a specified anatomical feature of the foot.

However, there is a simpler and potentially much less expensive method not described in the prior art that can be used to determine the position of the moving treadmill belt in relation to a specified anatomical feature of the foot. In accordance with this novel method, a plurality of independent contact actuated devices are placed at predetermined locations on the foot. Alternatively, the subject wears a shoe with a plurality of independent contact actuated devices mounted at predetermined locations on the sole of the shoe. Each contact actuated device is designed to undergo a measurable change in state when a point in the near vicinity of its mounting location on the foot comes in contact with the treadmill belt surface.

Contact actuated devices are mounted at points of likely first contact with the treadmill belt surface at the time of heel-strike. A normal adult individual is most likely to contact the surface with the heel of the foot during walking, or the rear most portion of the sole when shoes are worn. During running, a normal individual may contact the surface at the heel first, or may contact with the ball of the foot. In individuals with orthopedic deformities of the foot or neuromuscular disorders, in contrast, the first point of contact may be the heel of the foot, the ball of the foot, the toes, the medial edge of the foot, or its lateral edge. When shoes are worn, the point of first contact may be any point along the perimeter of the sole.

After the mounting points of the contact actuated devices have been selected in accordance with the above described criteria, the position of each contact actuated device is determined in relation to each of the specified anatomical features of the foot. The following methods are then used to determine the position of the treadmill belt in relation to coordinates of each of the specified anatomical features of the foot: (1) The position of the center of force at the time of heel-strike, initially determined in coordinates of the forceplate, is determined in relation to coordinates of the moving treadmill belt using methods described in the section "Analysis of Support Surface Reaction Forces". (2) Signals from the plurality of contact actuated devices associated with the heel-strike foot are monitored on a continuous basis beginning at the time of heel-strike to determine the first to indicate a contact induced change in state. (3) At the time of heel-strike, the locations of (a) the center of force and (b) the first contact actuated device to indicate a change of state are determined to be the same position in absolute terms. (4) For each specified anatomical feature of the foot, the difference when the same absolute position determined in step 3 is expressed in coordinates of the moving treadmill belt and in coordinates of the specified anatomical feature is determined. For each specified anatomical feature, the associated difference quantity is used to transform the center of force position quantity from coordinates of the moving treadmill belt to coordinates of the specified anatomical feature. Because the position of the foot in relation to the moving treadmill belt does not change from the time of heel-strike to the subsequent toe-off of that foot, the difference quantities specified at the time of heel-strike may be used throughout the step until the subsequent toe-off of the foot.

Figure 14:
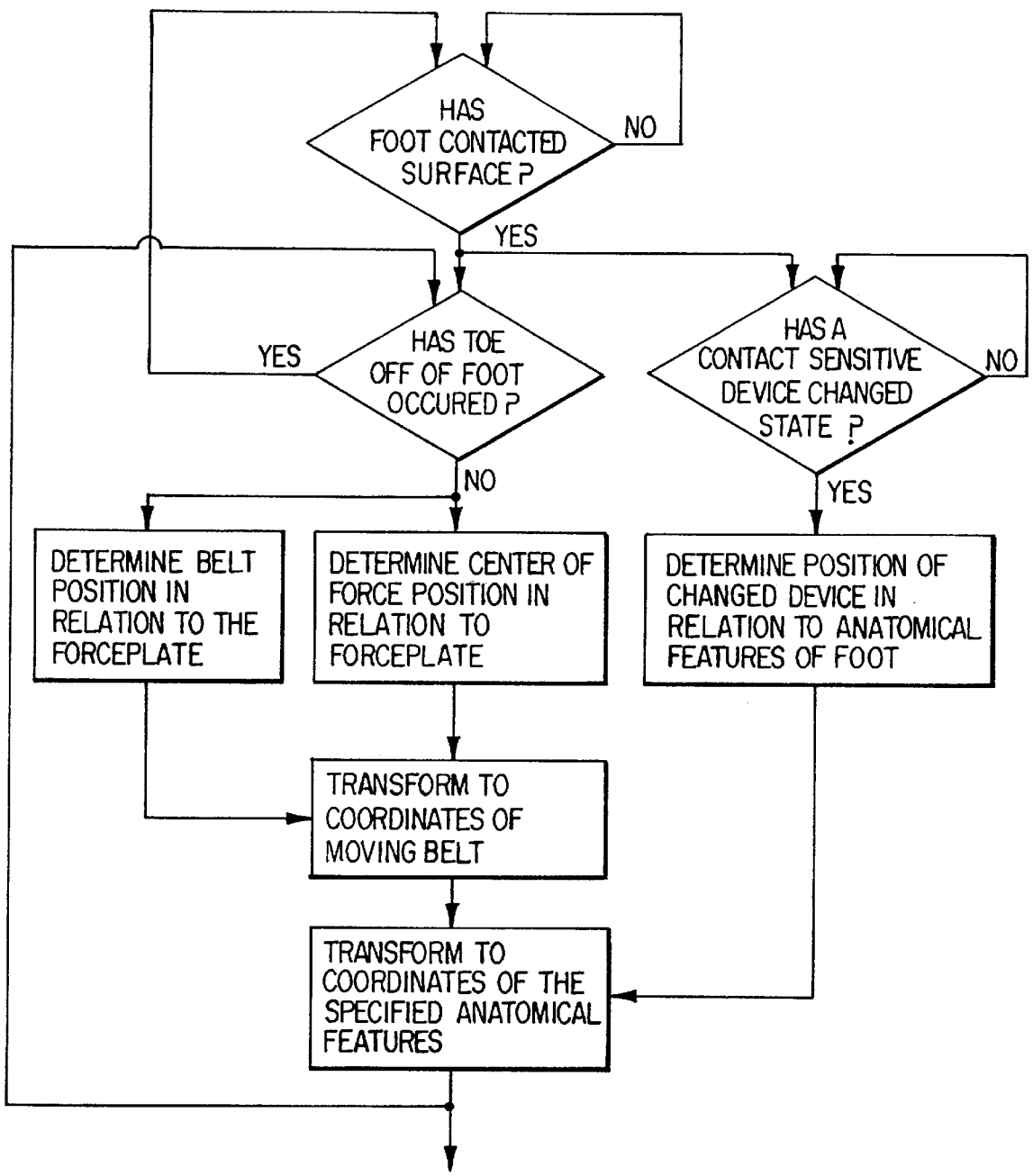
FIG. 14 shows a logic structure for determining the position of the center of force in relation to coordinates of the specified anatomical features of the foot.
Figure 15A:
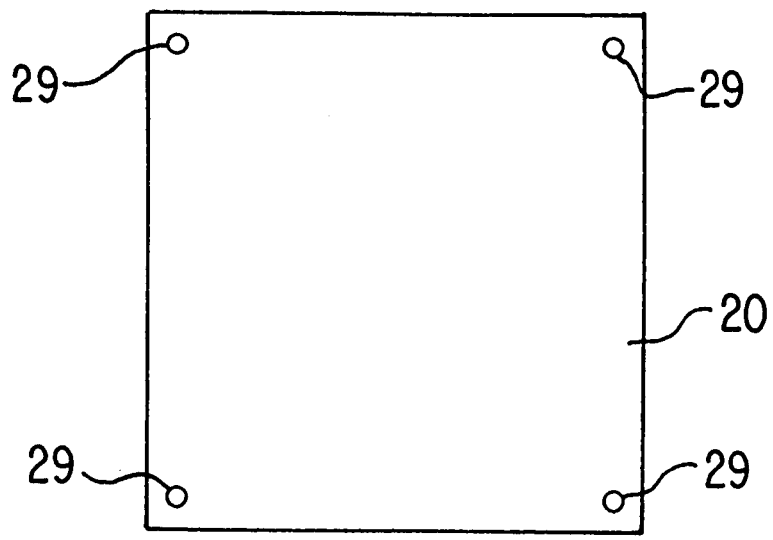
FIGS. 15A and 15B are schematics of prior-art forceplates that may be used in the embodiments of the invention that use forceplates.
Figure 15B:
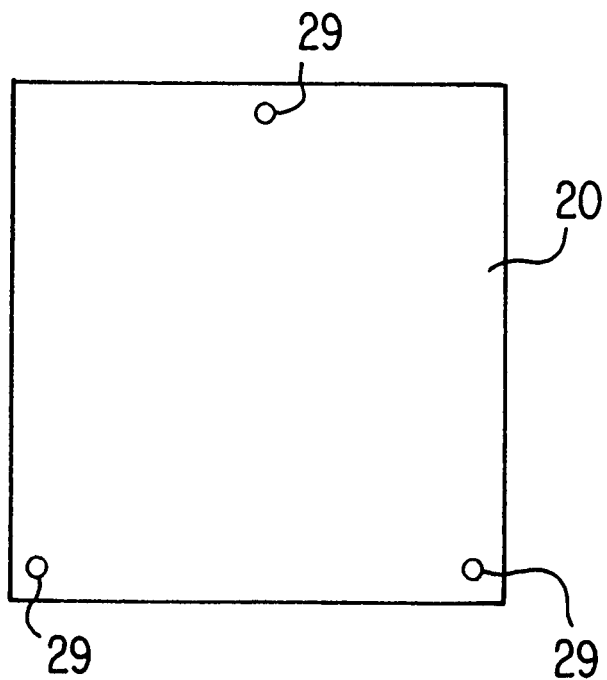

The flow chart of FIG. 14 shows the computer operations necessary to determine the position of the center of force in relation to coordinates of the specified anatomical features on a continuous basis. The computer identifies the occurrence of a heel-strike event using methods specified in the first preferred embodiment. At the time of heel-strike, the computer determines the position of the center of force of the striking foot in coordinates of the fixed forceplates and at the same time identifies the first contact sensitive transducer on the striking foot to indicate a change of state. Based on input from the treadmill belt position measuring system described previously, the computer determines on a continuous basis the position of the moving treadmill belt in relation to the fixed forceplate surface and the position of the center of force in relation to coordinates of the moving treadmill belt until the subsequent toe-off of the foot. Based on knowledge that the positions of the center of force at heel-strike and the first contact sensitive transducer to undergo a change of state are the same position at the time of heel-strike, the computer determines once for the step cycle from heel-strike to toe-off the position of the treadmill belt in relation to the specified anatomical features of the foot. Until the subsequent toe-off of the foot, the computer determines on a continuous basis the center of force position in relation to coordinates of the specified anatomical feature.

The accuracy of the above specified novel method will be determined by the numbers, locations, and sensitivities of the foot or shoe mounted contact activated devices. A simple embodiment of this method appropriate for normal adult subjects during walking and running uses two pressure actuated on-off switches, one mounted on the heel and one on the ball of each foot. The first switch to change state following heel-strike determines whether the heel or ball of the foot has contacted the surface of the treadmill belt first. A second embodiment which is more appropriate for patients with orthopedic deformities and/or musculoskeletal abnormalities uses four independent pressure sensitive devices, two mounted on the left and right sides of the heel of the foot and two mounted on the left and right sides of the ball of the foot. More complex embodiments use a plurality of contact actuated devices mounted at regular intervals around the perimeter of the foot.

Algorithm 1: Method for Identifying Heel-Strike and Toe-off Events During a Locomotor Activity A first computational algorithm makes use of the following definitions of events during performance of the locomotor activity. Each point in time at which the left or right foot makes initial contact with the treadmill belt surface at the beginning of a step is hereinafter termed a "left heel-strike" or "right heel-strike" event, respectively. Each point in time at which the left or right foot is lifted off the treadmill belt surface at the termination of a step is hereinafter termed a "left toe-off" or "right toe-off" event, respectively.

In the first preferred embodiment of the apparatus of the invention, an array of mechanically independent force transducers is positioned beneath the treadmill belt. In this embodiment, when the subject performs a specified locomotor activity on the treadmill belt, the following design criteria must be met:

(1) The combined areas of the transducers must underlay all areas of the treadmill belt which are contacted by a subject's foot at some point in time during the specified locomotor activity, (2) At each heel-strike event, the transducer underlying the treadmill belt area of the striking heel is not simultaneously underlying a belt area in contact with the other foot, (3) At each toe-off event, the transducer underlying the treadmill belt area of the toe-off is not simultaneously underlying a belt area in contact with the other foot.

FIGS. 3 and 4 show how the above criteria constrain the specified activity and the dimensions of the array of transducers (FIG. 3) or of the two forceplates (FIG. 4). To insure that condition 1 is met, the anteroposterior dimension of the area covered by the array of transducers or the two forceplates must be greater than the length of the subject's stride, while the lateral dimension must be greater than the width of the subject's stride.

FIG. 3 shows that the constraints imposed on walking activity by conditions 2 and 3 depend on the total number of independent force transducers. Areas 31 and 32, shown cross-hatched, indicate transducers experiencing a non-zero force. Conditions 2 and 3 place no additional constraints on the walking activity when the total number of force transducers is sufficiently large that the contact area of each foot can be independently recognized with the two feet directly adjacent to one another. In FIG. 3 either one or both of a anteroposterior row of transducers 33 and a lateral row of transducers 34 experiencing zero force separate the left foot contact area 32 from the right foot contact area 31. FIG. 4 shows the position of the feet in a "walking, double support right foot leading" position on the heel-strike forceplate 21 and the toe-off force plate 22 of FIG. 2. It can be seen that neither foot straddles the line 41 separating the two forceplates. As can be seen from FIG. 4, conditions 2 and 3 place the greatest constraint on the walking activity when the number of independent force transducers is two. Constraints imposed by a system having two independent forceplates are described further herein below. When the subject performs a specified running activity, conditions 2 and 3 place no additional constraints, since the two feet are never simultaneously in contact with the surface of the treadmill belt. A short-stride or shuffling gait wherein both feet contact the same lateral row of transducers (see row 111 in FIG. 11A) may be characterized by an apparatus according to the first embodiment of the invention if the feet are sufficiently spaced apart such as to maintain a anteroposterior row of transducers (see row 114 in FIG. 11A) in the zero force state.

Figure 5:
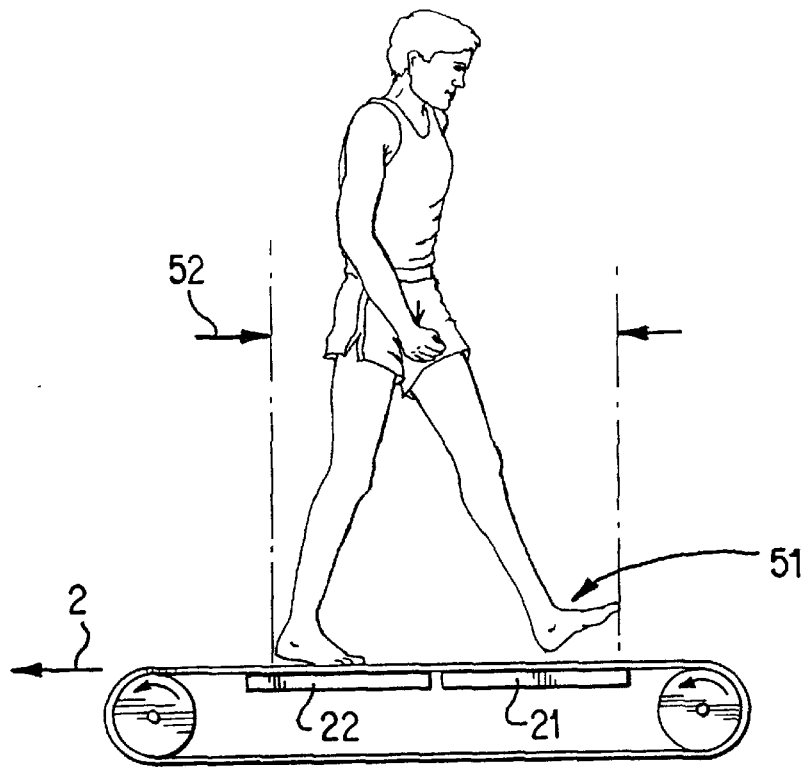
FIG. 5 shows a heel-strike event, walking.
Figure 6:
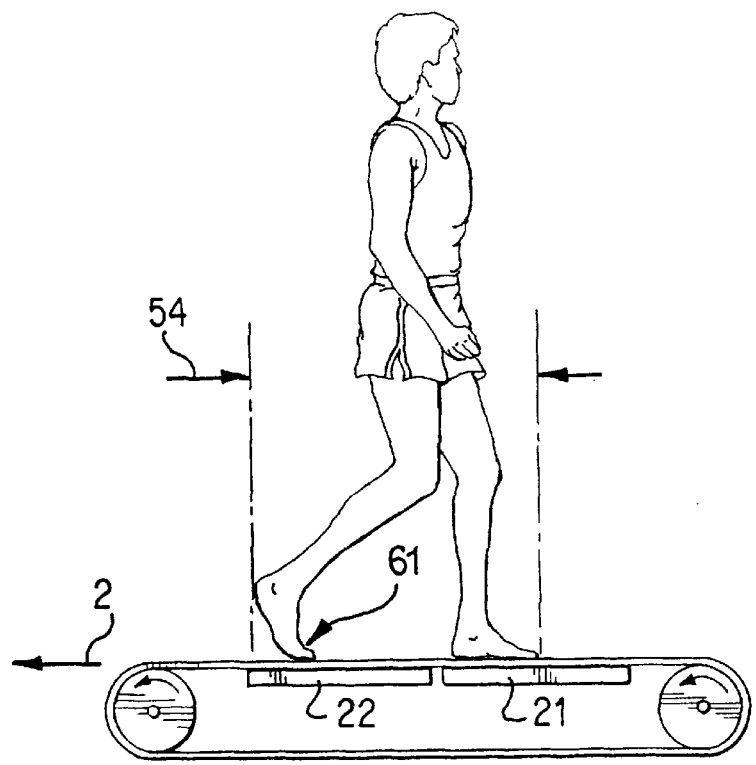
FIG. 6 shows a toe-off event, walking.
Figure 7:
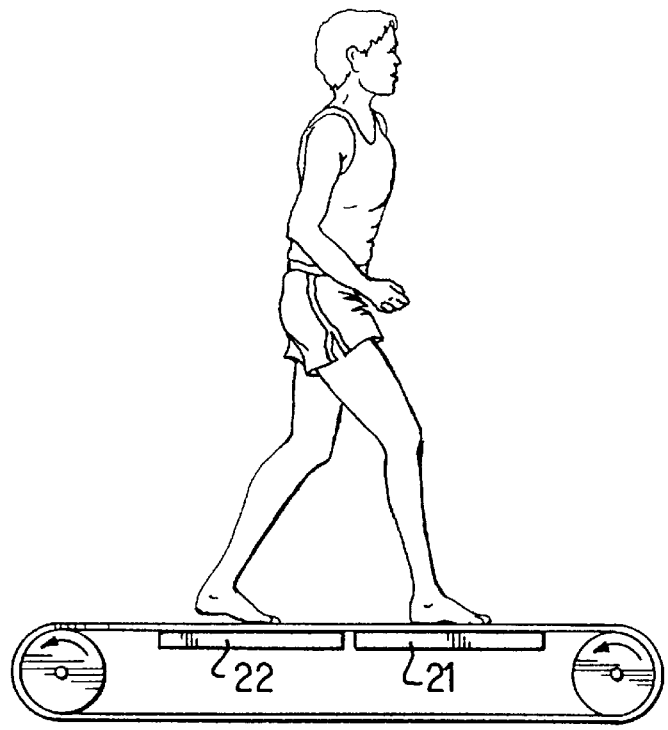
FIG. 7 show a double support phase.
Figure 8:
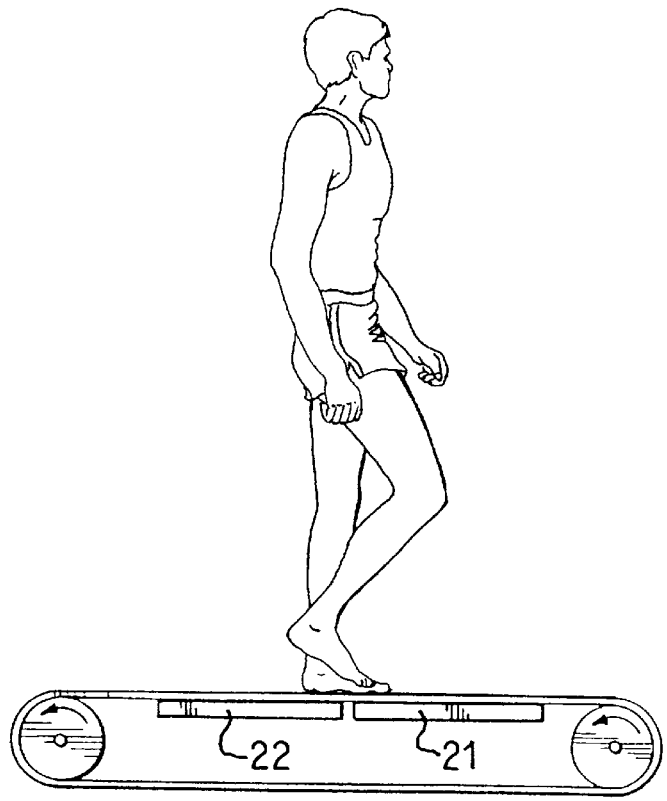
FIG. 8 shows a single support phase.

FIGS. 5, 6, 7 and 8 illustrate events and phases of walking on a treadmill such as illustrated in FIG. 2. FIG. 5 illustrates a heel-strike event, walking, with the heel of the foot (or shoe) striking the belt surface first. FIG. 6 illustrates a toe-off event, walking, with the toes the last point to contact the surface. FIGS. 7 and 8 illustrate double support phase and single support phase respectively. FIGS. 5 and 6 show the position of the subject's feet relative to the heel-strike forceplate 21 and the toe-off forceplate 22 at heel-strike 51 and toe-off 61 event times. The subject's feet remain within the area of the treadmill belt overlying one of the lower forceplates. At heel-strike and toe-off events, each foot is in contact with an area of the treadmill belt overlying only one forceplate. There is no overlap between the feet. Also shown are the direction of belt motion 2 and the length of subject's stride 52. FIGS. 7 and 8 show the position of the subject's feet relative to the heel-strike forceplate 21 and the toe-off forceplate 22 during double support and single support phases of the step cycle respectively. During all times of the double support phase, each foot contacts areas of only one forceplate and the two feet do not overlap. During the single support phase, the supporting foot may contact areas of either one or both forceplates.

Figure 9:
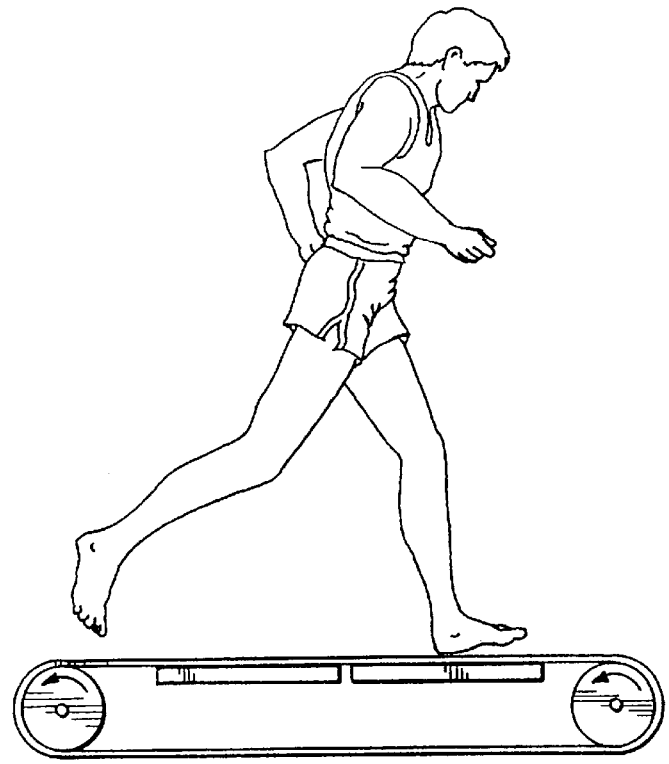
FIG. 9 shows a heel-strike event, running.
Figure 10:
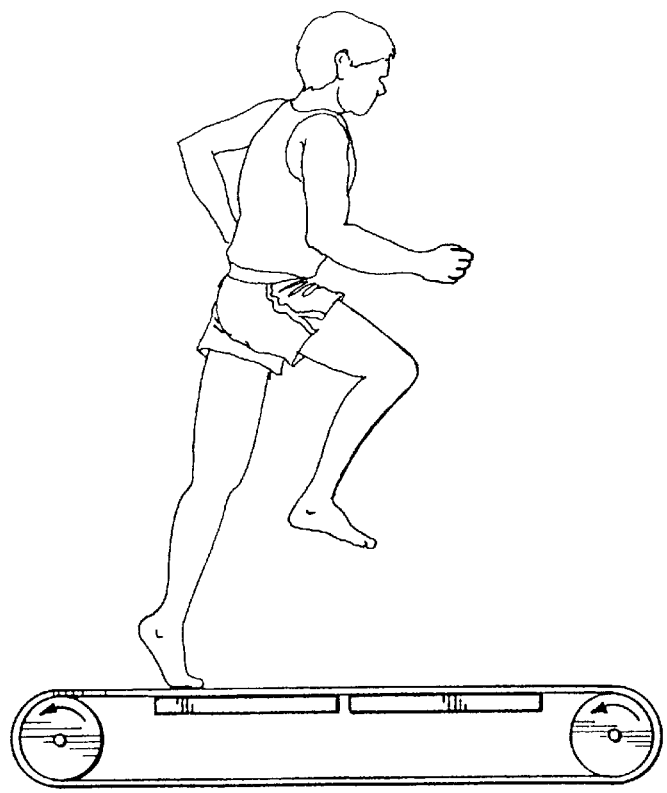
FIG. 10 shows a toe-off event, running.

FIGS. 9 and 10 illustrate, respectively, the heel-strike event during running and the toe-off event during running. At no time during running, are both feet simultaneously in contact with the belt surface.

Figures 11A, 11B:
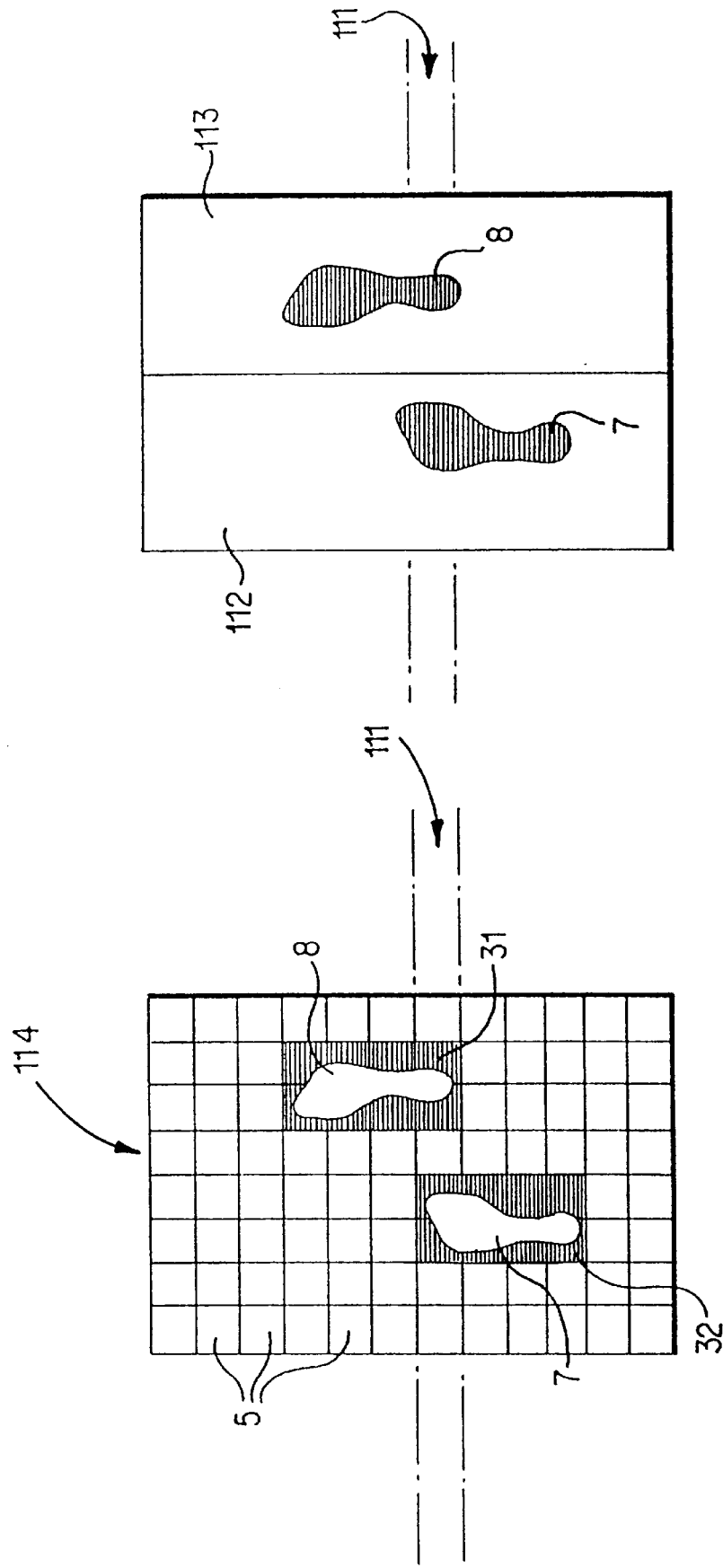
FIG. 11A shows a short-stride gait imposed on a treadmill with multiple transducers underneath the moving belt.
FIG. 11B shows a short-stride gait imposed on a treadmill with two forceplates underneath the moving belt.

FIGS. 11A and 11B show the situation of a gait shorter than 2 times the length of the foot so that feet overlap within a band 111. The embodiment of FIG. 11A is the same as the embodiment of FIGS. 1 and 3. The embodiment of FIG. 11B in an embodiment in which two forceplates (112 and 113) are oriented laterally with respect to the direction of movement of the belt.

Figure 12:
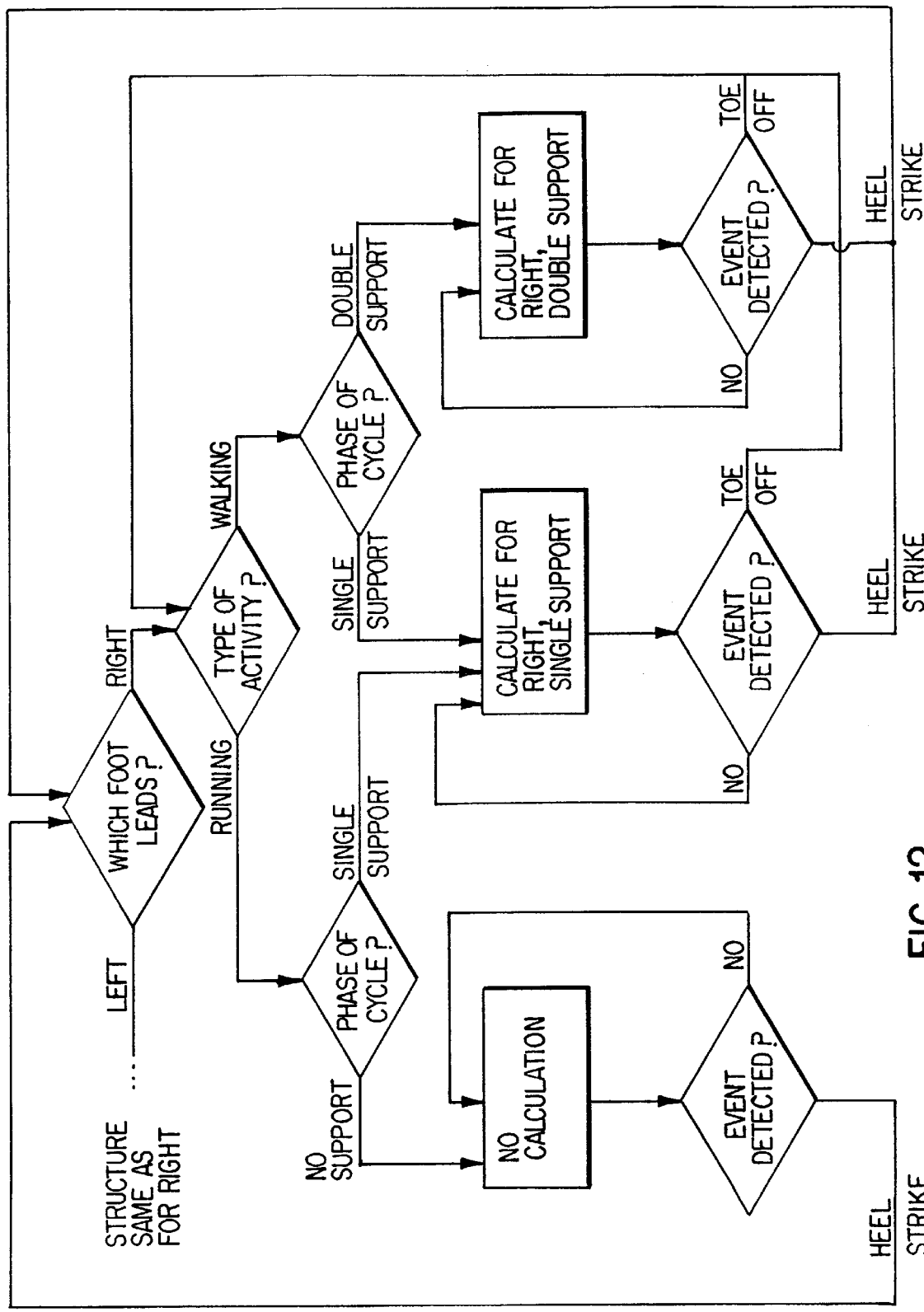
FIG. 12 shows a logic structure for associating a given force measurement with a specific phase of activity.

FIG. 12 shows a logic structure for associating a given force measurement with a specific foot and with a specific phase of a specific type of activity (walking or running).

Using the first preferred embodiment of the invention, heel-strike events and toe-off events may be identified by the following steps:

(1) Output signals from the transducers are processed on a continuous basis to identify, for each point in time, the anteroposterior position of the foremost transducer and the rearmost transducer which are measuring vertical component of force greater than zero.

(2) Heel-strike events are identified at each point in time when the anteroposterior position of the foremost transducer determined by step 1 is located a greater distance forward than the foremost transducer determined by step 1 for the immediately preceding point in time.

(3) Toe-off events are identified at each point in time when the anteroposterior position of the rearmost transducer determined by step 1 is located a greater distance forward than the rearmost transducer determined by step 1 for the immediately preceding point in time.

In the second preferred embodiment of the apparatus of the invention, two independent forceplates are positioned beneath the treadmill belt. In this embodiment, when the subject performs a specified locomotor activity on the treadmill belt, the following criteria must be met:

(1) The dimensions and placement of the two forceplates are such that the combined areas of the two underlay all areas of the treadmill belt which are contacted by a subject's foot at some point in time during the locomotor activity.

(2) During each heel-strike event, the foot makes initial contact with areas of the treadmill belt overlying the Heel-Strike forceplate (3) In the interval of time just preceding the initiation of each step, neither foot contacts areas of the treadmill belt overlying the Heel-Strike forceplate for a measurable period of time.

(4) Just prior to each toe-off event, the foot makes final contact with areas of the treadmill belt overlying the Toe-Off forceplate.

(5) Immediately following termination of each step, neither foot is in contact with the Toe-Off forceplate for a measurable period of time.

FIGS. 5–10 show how these five performance criteria constrain the specified locomotor activity when two independent forceplates are used. To insure that condition 1 is met, the combined anteroposterior dimension of the two forceplates must be greater than the length of the subject's stride, while the combined lateral dimension is greater than the width of the subject's stride. Conditions 2 and 4 require that the subject's anteroposterior position on the treadmill belt is maintained sufficiently centered above the two forceplates such that heel-strike and toe-off events occur on areas of the treadmill belt above their respective Heel-Strike and Toe-Off forceplates. When the subject is performing a specified walking activity, conditions 3 and 5 require that the subject's stride length is sufficiently long compared to the foot length such that only one foot is in contact with areas of the treadmill belt overlying the Heel-Strike and Toe-Off forceplates at the time of heel-strike and toe-off events, respectively. During performance of a specified running activity, conditions 3 and 5 place no additional constraints on the activity, since the two feet are never simultaneously in contact with the treadmill belt.

Using the second preferred embodiment of the apparatus of the invention (FIG. 2), a heel-strike event is identified as each point in time at which the magnitude of the vertical component of force exerted on the Heel-Strike forceplate increases above a zero value after having been at a zero value for a measurable period of time. A toe-off event is identified as the first point in time, following each identified heel-strike event, at which the magnitude of the vertical component of force exerted on the Toe-Off forceplate diminishes to a zero value after having been greater than a zero value for a measurable period of time.

Using either algorithm with either embodiment of the invention, a heel-strike event is identified as left or right according to the following steps:

(1) If fewer than a specified even number of heel-strike events have been identified since beginning the locomotor task, the heel-strike event is not classified as to left or right.

(2) Upon occurrence of the specified even number of identified heel-strike events, the lateral positions of the center of vertical force determined at the time of each heel-strike event are averaged separately for the odd and the even numbered heel-strike events.

(3) The odd numbered heel-strike events are classified as left (or right), depending on whether the average lateral position of the center of force at the time of the odd numbered heel-strikes determined in step 2 is to the left (or right) of the average lateral position of the center of force at the time of the even numbered heel-strikes.

(4) The even numbered heel-strike events are classified as the opposite right (or left) foot opposite compared to the odd numbered heel-strike events.

(5) All odd and even heel-strike events beyond the number specified in step 2 are classified as left or right in accordance with the odd and even relations determined in steps 3 and 4.

Specification of the even number of heel-strike events used to classify heel-strikes as left or right will determine the statistical reliability of the classification method. The larger the even number used, the more reliable will be the classification. The even number required to meet an given accuracy criteria for left and right classification can be calculated experimentally by determining in a population of subjects the lateral positions of the center of vertical force at the time of left and right heel-strikes during a sequence of steps and then determining the percentage of left and right foot steps meeting the criteria that the lateral positions of the center of vertical force for the left foot at the time of left heel-strikes are located to the left of the position of the center of vertical force for the right foot at the time of right heel-strikes.

Algorithm 2: Method for Identifying the Specified Locomotor Activity as Walking or Running Using the first preferred embodiment of the apparatus of the invention, the locomotor activity is identified as either walking or running by the following criteria: (1) The activity is walking if the magnitude of a total vertical force component determined by summing the magnitudes of the vertical force components measured by each of the plurality of force transducers is greater than zero for all points in time beginning with the second most recent heel-strike event and ending at the present time. (2) The activity is running if the magnitude of a total vertical force component determined by summing the magnitudes of the vertical force components measured by each of the plurality of force transducers diminishes to a zero value for some measurable period of time greater than zero during the period beginning with the second most recent heel-strike event and ending at the present time.

Using the second preferred embodiment of the apparatus of the invention, the locomotor activity is identified as either walking or running by the following criteria: (1) The activity is walking if the magnitude of a total vertical force component determined by summing the magnitudes of the vertical force components measured by each of the two forceplates is greater than zero for all points in time beginning with the second most recent heel-strike event and ending at the present time. (2) The activity is running if the magnitude of a total vertical force component determined by summing the magnitudes of the vertical force components measured by each of the two forceplates diminishes to a zero value for some measurable period of time greater than zero during the period beginning with the second most recent heel-strike event and ending at the present time.

Algorithm 3: Method for Identifying the Phases of a Locomotor Activity

The four phases of a walking activity are described as follows:

(1) double support phase with the left foot leading,
(2) single support phase with the left foot,
(3) double support phase with right foot leading, and
(4) single support phase with right foot.

Using either embodiment of the apparatus of the invention, the four phases of a walking activity are identified by the following criteria:

(1) Double support phase with left foot leading—begins at the left heel-strike event and ends at the right toe-off event.
(2) Single support phase with the left foot—begins at right toe-off event and ends with the right heel-strike event.
(3) Double support phase with right foot leading—begins at right heel-strike event and ends at the left toe-off event.
(4) Single support phase with right foot—begins at left toe-off event and ends at the left heel-strike event.

The four phases of running activity are described as follows:

(1) single support phase with the left foot,
(2) no support phase,
(3) single support phase with the right foot, and
(4) no support phase.

Using either embodiment of the invention, the above four phases of a running activity are identified by the following criteria:

(1) Single support phase with left foot—begins at the left heel-strike event and ends at the left toe-off event.
(2) No support phase—begins at left toe-off event and ends with right heel-strike event.
(3) Single support phase with right foot—begins at right heel-strike event and ends at the right toe-off event.
(4) No support phase—begins at the right toe-off event and ends at the left heel-strike event.

Algorithm 4: Method for Determining Independent Quantities Related to the Forces Exerted by Each Foot in Relation to Coordinates of the Force Measuring System Using the first preferred embodiment of the apparatus of the invention (FIG. 1), quantities related to the forces exerted on the force transducers are attributed to the forces exerted on the overlying treadmill belt by each of the left and right feet in accordance with the following preferred algorithm:

I. Activity Identified as Walking
   (1) Phase identified as double support left foot
       (a) inputs from the transducers are processed to identify two non-contiguous groups of transducers, each group being comprised of one or more contiguous transducers measuring vertical force quantities greater than zero (see FIG. 3).
       (b) quantities related to the position and the magnitude of the center of force are determined separately for each of the two groups of transducers specified in step 1(a) above.
       (c) position and magnitude quantities determined for the foremost of the two groups of contiguous transducers identified in step 1(b) above are attributed to the forces exerted by the left foot.
       (d) position and magnitude quantities determined for the rearmost of the two groups of contiguous transducers identified in step 1(b) above are attributed to the forces exerted by the right foot.
   (2) Phase identified as single support left foot
       (a) quantities related to the position and magnitude of the center of force are determined from the combined force measures from all of the transducers.
       (b) position and magnitude quantities identified in step 2(a) above are attributed to the force exerted by the left foot.
   (3) Phase identified as double support right foot
       (a) inputs from the transducers are processed to identify two non-contiguous groups of transducers, each group being comprised of one or more contiguous transducers measuring vertical force quantities greater than zero.
       (b) quantities related to the position and the magnitude of the center of force are determined separately for each of the two groups of transducers specified in step 3(a) above.
       (c) position and magnitude quantities determined for the foremost of the two groups of contiguous transducers identified in step 3(b) above are attributed to the forces exerted by the right foot.
       (d) position and magnitude quantities determined for the rearmost of the two groups of contiguous transducers identified in step 3(b) above are attributed to the forces exerted by the left foot.
   (4) Phase identified as single support right foot
       (a) quantities related to the position and magnitude of the center of force are determined from the combined force measures from all of the transducers.

(b) position and magnitude quantities identified in step 4(a) above are attributed to the force exerted by the right foot.

II. Activity Identified as Running (1) Phase identified as single support left (a) quantities related to the position and magnitude of the center of force are determined from the combined force measures from all of the transducers.

(b) position and magnitude quantities identified in step 1(a) above are attributed to the force exerted by the left foot.

(2) Phase identified as single support right (a) quantities related to the position and magnitude of the center of force are determined from the combined force measures from all of the transducers.

(b) position and magnitude quantities identified in step 2(a) above are attributed to the force exerted by the right foot.

Using the second preferred embodiment of the apparatus of the invention (FIG. 2), quantities related to the position and magnitude of the center of vertical force exerted on each of the heel-strike and toe-off forceplates are attributed to the forces exerted on the overlying treadmill belt by the left foot or by the right foot in accordance with the following preferred algorithm:

I. Activity Identified as Walking (1) Phase identified as double support left foot leading (a) quantities related to the position and magnitude of the center of force are determined independently for the forces exerted on the heel-strike and the toe-off forceplates.

(b) position and magnitude quantities determined for the heel-strike forceplate in step 1(a) above are attributed to the forces exerted by the left foot.

(c) position and magnitude quantities determined independently for the toe-off forceplate are attributed to forces exerted by the right foot.

(2) Phase identified as single support left foot (a) quantities related to the position and magnitude of the center of force are determined for the combined forces exerted on the heel-strike and toe-off forceplates.

(b) position and magnitude quantities determined in step 2(a) above are attributed to the left foot.

(3) Phase identified as double support right foot leading (a) quantities related to the position and magnitude of the center of force are determined independently for the forces exerted on the heel-strike and toe-off forceplates.

(b) position and magnitude quantities determined for the heel-strike forceplate in step 3(a) above are attributed to the forces exerted by the right foot.

(c) position and magnitude quantities determined independently for the toe-off forceplate are attributed to forces exerted by the left foot.

(4) Phase identified as single support right foot (a) quantities related to the position and magnitude of the center of force are determined for the combined forces exerted on the heel-strike and toe-off forceplates.

(b) position and magnitude quantities determined in step 4(a) above are attributed to the right foot.

II. Activity Identified as Running (1) Phase identified as single support left foot (a) quantities related to the position and magnitude of the center of force are determined for the combined forces exerted on the heel-strike and toe-off forceplates.

(b) position and magnitude quantities determined in step 1(a) above are attributed to the left foot.

(2) Phase identified as single support right foot (a) quantities related to the position and magnitude of the center of force are determined for the combined forces exerted on the heel-strike and toe-off forceplates.

(b) position and magnitude quantities determined in step 2(a) above are attributed to the right foot.

Algorithm 5: Method for Determining Independent Quantities Related to the Forces Exerted by Each Foot in Relation to Coordinates of the Movable Treadmill Belt Using either embodiment of the apparatus of the invention, quantities related to the position of the center of force exerted by each foot in relation to coordinates of the force measuring system (determined using algorithms 1 through 4) are transformed into quantities related to position in relation to coordinates of the treadmill belt by the following steps:

(1) A quantity related to the time dependent anteroposterior position of the treadmill belt is determined on a continuous basis from the belt position measuring system.

(2) A quantity related to the time dependent anteroposterior position of the center of force in coordinates of the treadmill belt is determined by summing a quantity related to the time dependent position of the center of force in coordinates of the force transducers with a quantity related to the time dependent position of the treadmill belt determined in step 1.

(3) A quantity related to the time dependent lateral position of the center of force in coordinates of the treadmill belt is determined to be identical to a quantity related to the time dependent lateral position of the center of force in coordinates of the force transducers, since the treadmill belt is not movable in the lateral direction.

Algorithm 6: Method for Determining Independent Quantities Related to the Forces Exerted by Each Foot in Relation to Specified Anatomical Features of the Foot Using the first preferred embodiment of the apparatus of the invention (FIG. 1), quantities related to the position of the center of force in relation to the coordinates of the force transducers are transformed into quantities related to position of the center of force in relation to a specified anatomical feature of the foot using the following steps:

(1) Beginning with each heel-strike event and continuing until the next toe-off event for the same foot, the group of contiguous transducers measuring vertical quantities of force greater than zero due to the forces exerted by the foot in question is identified in accordance with methods specified in Algorithm 4.

(2) The group of transducers identified in step 1 above is analyzed to determine the time dependent positional dimensions of the area of contact between the foot specified in step 1 in relation to the transducers.

(3) The positional relations between a specified anatomical feature of the foot and dimensions of the area of contact between the foot and the support surface during standing is specified on a statistical basis for feet of different dimensions.

(4) The time dependent position of the specified anatomical feature of the foot specified in step 1 in relation to coordinates of the force transducers is calculated by comparing the positional dimensions of the area specified in step 2 with the positional dimensions specified in step 3.

(5) The quantity related to the position and magnitude of the center of force exerted by the foot specified in step 1 in relation to the specified anatomical feature of the foot is the time dependent difference between the position of the anatomical feature determined in step 4 and the position of the center of force determined by Algorithm 4.

Using the third preferred embodiment of the apparatus of the invention, a quantity related to the position of the center of force is transformed from coordinates of the fixed transducers to coordinates of the specified anatomical feature of the foot using the following steps:

(1) Independent pressure sensitive switches are mounted on the heel and the ball of each foot at the likely first points of contact with the surface of the treadmill belt during heel-strike.

(2) For each pressure sensitive switch, the position of the mounting point on the foot is determined in relation to the specified anatomical feature of the foot.

(3) Beginning with each heel-strike event and continuing until the next toe-off event for the foot in question, a quantity related to the position of the center of force exerted by the foot in question in relation to coordinates of the force measuring system is determined by methods in accordance with Algorithm 4.

(4) A quantity related to the position of the center of force in relation to coordinates of the force measuring system determined by step 3 is transformed into a position quantity expressed in coordinates of the moving treadmill belt using methods in accordance with Algorithm 5.

(5) Beginning with each heel-strike event, the output states of the two pressure sensitive switches mounted on the striking foot in accordance with step 1 are monitored on a continuous basis to determine the first switch indicating a change of state.

(6) A quantity related to the position of the moving treadmill belt in relation to the position of the specified anatomical feature of the foot is determined by summing a quantity related to the position of the center of force at the time of heel-strike as determined in step 3 and a quantity related to the position of the first pressure sensitive switch to change state following the heel-strike in relation to the specified anatomical feature as determined in step 2.

(7) A quantity related to the position of the center of force in coordinates of the moving treadmill belt is transformed into a position quantity in coordinates of the specified anatomical feature of the foot using the quantity related to the position of the center of force in relation to coordinates of the moving treadmill belt as specified in step 4 and the quantity related to the position of the moving treadmill belt in relation to the specified anatomical feature of the foot as specified in step 6.

What is claimed is:

1. An apparatus for characterizing the gait of a subject comprising:

(a) a treadmill having a substantially planar tread area and movable support surface capable of moving in the plane of the tread area;

(b) two forceplates, each forceplate producing an output signal and being associated with a portion of the tread area, and mounted in a fixed position beneath the movable support surface laterally oriented with respect to the direction of movement, in such a way as to permit motion of the support surface across such forceplate and to permit such forceplate to receive substantially all of the vertical force exerted by the subject's foot on the portion of the tread area, wherein each of the forceplates includes a flat, rigid surface that couple at least three force transducers, and wherein each of the forceplates measures the position and magnitude of the center of force exerted on that forceplate; and (c) computational means for accepting the output signals and providing quantities related to the forces exerted by each foot on the movable support surface.

2. An apparatus according to claim 1, further including contact sensitive transducer means, disposed in fixed relation to the subject's foot, for providing signals indicative of heel-strike to the computational means.

3. A method for characterizing the locomotor activity of a subject comprising:

(A) placing the subject in a position of locomotion on a movable support surface having a tread area;

(B) providing two forceplates, each forceplate producing an output signal and being associated with a portion of the tread area, and mounted in a fixed position beneath the movable support surface laterally oriented with respect to the direction of movement, in such a way as to permit motion of the support surface across such forceplate and to permit such forceplate to receive substantially all of the vertical force exerted by the subject's foot on the portion of the tread area, wherein each of the forceplates includes a flat, rigid surface that couple at least three force transducers, and wherein each of the forceplates measures the position and magnitude of the center of force exerted on that forceplate;

(C) instructing the subject to perform locomotion on the movable surface;

(D) accepting the output signal from each forceplate, at each of a series of points in time, during a period of time; and (E) processing the output signals to provide quantities related to the vertical forces exerted by each foot on the movable support surface.

4. An apparatus for characterizing the gait of a subject performing a locomotor activity on a substantially planar tread area, the apparatus comprising:

a treadmill having a movable support surface capable of moving in a direction of travel the plane of the tread area, upon which the subject applies forces with both feet;

a matrix of force transducers, each transducer producing an output signal and being associated with a portion of the tread area directly above the transducer, so that every portion of the tread area on which a foot of the subject may exert a force has a transducer associated with it, each portion of the tread area having an area less than the area of the soles of the feet of an average adult human, the matrix of force transducers being arranged in a grid, n transducers wide by m transducers long, where both n and m are both greater than 1, the matrix of force transducers being mounted in a fixed position beneath the movable support surface in such a way as to permit the support surface across the matrix of force transducers and to permit each transducer to receive substantially all of the vertical force exerted by the subject's foot on the portion of the tread area associated with that transducer; and computational means for accepting the output signals and providing quantities related to the forces independently exerted by each foot on the movable support surface, and for characterizing the gait of the subject.

5. An apparatus according to claim 4, further including contact sensitive transducers, mountable in fixed relation to anatomical features of a foot of the subject, for providing to the computational means signals indicative of the position on the foot where a force is exerted by the foot onto the movable support surface, the force having a center, and wherein the computational means includes means for accepting the signals from the contact sensitive transducers and for determining the position of the center of force exerted by the foot on the movable support surface in relation to the anatomical features on a continuous basis.

6. An apparatus for characterizing the gait of a subject comprising:
  (a) a treadmill having a substantially planar tread area and movable support surface capable of moving in the plane of the tread area;
  (b) a plurality of force transducers, each transducer producing an output signal and being associated with a portion of the tread area, and mounted in a fixed position beneath the movable support surface in such a way as to permit motion of the support surface across such transducer and to permit such transducer to receive substantially all of the vertical force exerted by the subject's foot on the portion of the tread area; and
  (c) computational means for accepting the output signals and providing quantities related to the forces exerted by each foot on the movable support surface,
  wherein the plurality of force transducers consists of two forceplates anteroposteriorly oriented with respect to the direction of movement of the movable support surface.

* * * * *